United States Patent [19]

Suzuki

[11] Patent Number: Plant 7,139

[45] Date of Patent: Feb. 6, 1990

[54] ROSE PLANT—KIBOH VARIETY

[75] Inventor: Seizo Suzuki, Tokyo, Japan

[73] Assignee: The Conard-Pyle Company, West Grove, Pa.

[21] Appl. No.: 299,678

[22] Filed: Jan. 23, 1989

[51] Int. Cl.[4] ..... A01H 5/00

[52] U.S. Cl. ..... Plt./22

[58] Field of Search ..... Plt./22

*Primary Examiner*—Robert E. Bagwill

*Attorney, Agent, or Firm*—Burns, Doane, Swecker & Mathis

[57] ABSTRACT

A new and distinct variety of Floribunda rose plant is provided which abundantly and continuously forms attractive long lasting large very double bicolor blossoms. The blossoms are strawberry red with a lemon base on the inside and are lemon yellow tinted with turkey red on the outside. The plant is bushy and exhibits vigorous vegetation. The new variety is particularly well suited for the decoration of parks and gardens. Good resistance to cryptogamic diseases also is exhibited.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) of the new variety was the Liberty Bell variety (nonpatented in the United States). The male parent (i.e., the pollen parent) of the new variety was the Kagayaki variety (nonpatented in the United States). The parentage of the new variety can be summarized as follows:

Liberty Bell × Kagayaki.

The seeds resulting from the above pollination were sown and several small plants were obtained which were physically and biologically different from each other. Selective study resulted in the identification of a single plant of the new variety.

The new variety meets well the needs of the horticultural industry for all uses, and is particularly well suited for growing in parks and gardens. Well balanced plants are formed which are also well adapted for growing in containers.

It was found that the new variety of Floribunda rose plant of the present invention possesses the following combination of characteristics:

(a) forms attractive long lasting bicolor very double blossoms which are strawberry red with a lemon base on the inside and are lemon yellow tinted with turkey red on the outside,
(b) is particularly well suited for the decoration of parks and gardens, and
(c) exhibits a vigorous bushy growth habit.

The new variety undergoes asexual propagation by all routes, including budding, grafting, cuttage, etc. The characteristics of the new variety have been found to be strictly transmissible by such asexual propagation from one generation to another.

The new variety has been named the Kiboh variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were two years of age and observed during September while budded on *Rose froebelli* understock and growing outdoors at LeCannet-des-Maures, Var, France.

Figures 1, 2, 3, 4, 5, 6, 7, 8, 9, 10, 11, 12, 13, 14, 15, 16:
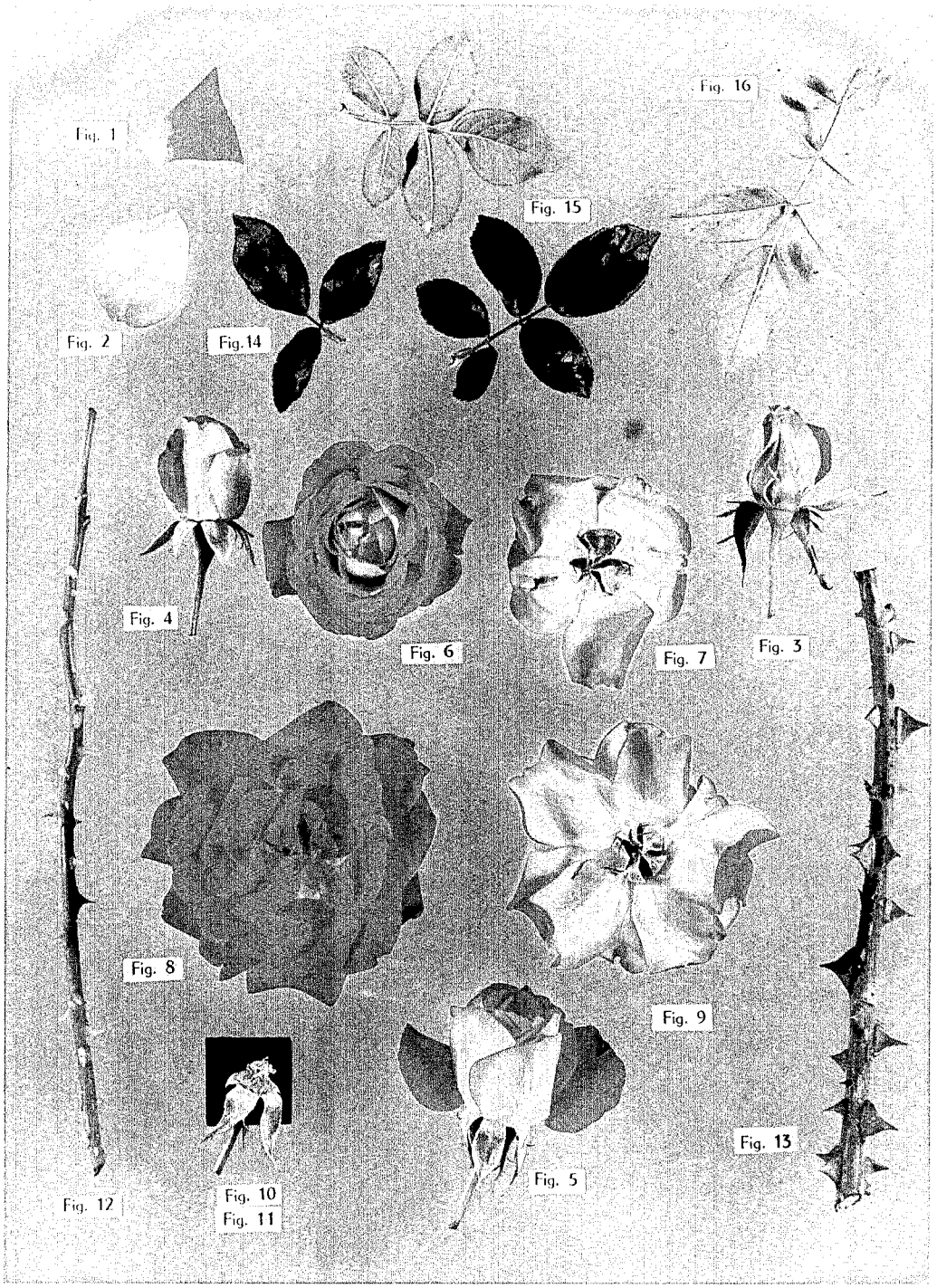
FIG. 1 illustrates a specimen of a petal viewed from the inside.
FIG. 2 illustrates a specimen of a petal viewed from the outside.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower—plan view—obverse.
FIG. 7 illustrates a specimen of a fully open flower—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.

FIGS. 10/11 illustrate a specimen of a floral receptacle showing the arrangement of the stamens and pistils;

FIG. 12 illustrates a specimen of a young flowering stem;

FIG. 13 illustrates a specimen of an adult main branch;

FIG. 14 illustrates a specimen of a leaf with three leaflets—upper surface;

FIG. 15 illustrates specimens of leaves with five leaflets—upper (bottom) and under (top) surfaces; and FIG. 16 illustrates a specimen of a leaf with seven leaflets—under surface.

DETAILED DESCRIPTION

The chart used in the identification of the colors is that of the Royal Horticultural Society (R.H.S. Colour Chart). The terminology which precedes reference to the chart has been added to indicate the corresponding color in more common terms. The description is based on two year old specimens of the new variety during September while grafted on *Rosa froebelli* understock and growing outdoors at LeCannet-des-Maures, Var France.

Class: Floribunda.

Plant:

*Height.*—Approximately 80 to 95 cm. on average.

*Habit.*—Bushy.

Branches:

*Color.*—Young stems: light green, Yellow-Green Group 146C. Adult wood: medium green, Yellow-Green Group 146B, Leaves:

*Stipules.*—Adnate, pectinate, very wide and linear.

*Petioles.*—Upper surface: striped, reddish brown on young foilage and medium green on adult foilage with more or less glandular edges. Under surface: light green, with a few crooked thorns.

*Leaflets.*—Number: 3, 5 (most often), and 7. Shape: pointed. Serration: simple and regular. General Appearance: foilage is bright, dense and plentiful. Color (young foilage): upper surface: reddish brown. under surface: reddish brown. Color (adult foilage): Upper surface: dark green, Yellow-Green Group 147A. under surface: medium green, Yellow-Green Group 147B.

Inflorescence:

*Number of flowers.*—Commonly 1 to 3 per stem.

*Peduncle.*—Short, straight, and rigid, approximately 4 to 5 cm. in length on average.

*Sepals.*—Upper surface: tomentose and greenish tinted with reddish brown in coloration. Under surface: light green in coloration more or less glandular, and the outside sepals have more or less appendiculated edges.

Buds.—Shape: pointed. Length: approximately 2.5 to 3 cm. on average. Size: average. Color upon opening: upper surface: guardsman red, Red Group 45A. under surface: cherry red, Red Group 45B with some tangerine orange, Orange Group 24C.

*Flower.*—Shape: cuplike and very double. Diameter: approximately 8 to 10 cm. on average. Color (when opening begins): upper surface: strawberry red, Red Group 46B, with lemon yellow, Yellow-Orange Group 14B at the base. under surface: lemon yellow, Yellow-Orange Group 14B, and edged with turkey red, Red Group 46C. Color (when blooming): upper surface: strawberry red, Red Group 46B, with lemon yellow, Yellow-Orange Group 14B at the base. under surface: lemon yellow, Yellow-Orange Group 14B, more or less tinted with turkey red, Red Group 46C. Color (at end of opening): upper surface: strawberry red, Red Group 46B, changing to delft rose, Red Group 46D. under surface: lemon yellow, Yellow Group 14B, more or less tinted with turkey red, Red Group 46C. Fragrance: none. Lasting quality: very long. Petal drop: the petals drop off cleanly. Petal number: approximately 41 to 47 on average. Petal texture: consistent. Petal form: broadly rounded at the tip. Stamen number: approximately 137 on average. Anthers: normal, light yellow in coloration. Filaments: orange yellow and of irregular heights. Pistils: approximately 95 on average. Stigmas: normal, yellowish in coloration. Styles: straw colored with fuchsine tips, pairs are often bonded together, and of irregular heights. Receptacle: light green, smooth, and in longitudinal section in the shape of a pitcher.

Development:

*Vegetation.*—Average.

*Blooming.*—Very floriferous eith continuous blooming.

*Aptitude to bear fruit.*—Good.

*Resistance to diseases.*—Good.

*Resistance to frost.*—Excellent.

I claim:

1. A new and distinct variety of Floribunda rose plant characterized by the following combination of characteristics:

(a) forms attractive long lasting bipolar very double blossoms which are strawberry red with a lemon yellow base on the inside and are lemon yellow tinted with turkey red on the outside, (b) is particularly well suited for the decoration of parks and gardens, and (c) exhibits a vigorous bushy growth habit;

substantially as herein shown and described.

* * * * *